(12) United States Patent  (10) Patent No.: US 8,151,634 B2
Lambert  (45) Date of Patent: Apr. 10, 2012

(54) DEVICE AND METHOD FOR DETECTING THE FROTHING ABILITY OF A FLUID

(75) Inventor: Noel William Alexander Lambert, Lower Belford (AU)

(73) Assignee: The University of Newcastle Research Associates Limited, New South Wales (AU)

( * ) Notice: Subject to any disclaimer, the term of this patent is extended or adjusted under 35 U.S.C. 154(b) by 591 days.

(21) Appl. No.: 12/306,598

(22) PCT Filed: Jun. 29, 2007

(86) PCT No.: PCT/AU2007/000903
§ 371 (c)(1),
(2), (4) Date: Dec. 24, 2008

(87) PCT Pub. No.: WO2008/000036
PCT Pub. Date: Jan. 3, 2008

(65) Prior Publication Data
US 2009/0283146 A1    Nov. 19, 2009

(30) Foreign Application Priority Data
Jun. 30, 2006   (AU) .............................. 2006903676

(51) Int. Cl.
*G01N 37/00* (2006.01)
(52) U.S. Cl. .................. 73/60.11; 73/61.41; 73/61.44
(58) Field of Classification Search ............... 73/60.11, 73/61.41, 61.44
See application file for complete search history.

(56) References Cited

U.S. PATENT DOCUMENTS

| 2,778,499 | A | * | 1/1957 | Chamberlain et al. | ........ | 209/166 |
| 3,027,755 | A | * | 4/1962 | Groll, Jr. et al. | ............. | 73/60.11 |
| 3,151,061 | A | * | 9/1964 | Orr | ............................... | 208/327 |
| 3,371,779 | A | * | 3/1968 | Hollingsworth et al. | ..... | 209/166 |
| 4,061,016 | A | * | 12/1977 | Noel et al. | .................... | 73/60.11 |
| 4,470,903 | A | * | 9/1984 | van Leeuwen | ................ | 209/168 |
| 4,477,338 | A | * | 10/1984 | Hellmann | ......................... | 209/5 |
| 4,621,521 | A | * | 11/1986 | Lattek et al. | ................. | 73/60.11 |
| 5,011,595 | A | * | 4/1991 | Meenan et al. | ............... | 209/166 |
| 5,022,984 | A | * | 6/1991 | Pimley et al. | ................. | 209/170 |
| 5,167,798 | A | * | 12/1992 | Yoon et al. | .................... | 209/170 |

(Continued)

FOREIGN PATENT DOCUMENTS

EP    0544428 A1    6/1993

(Continued)

OTHER PUBLICATIONS

International Search Report prepared by th Australian Patent Office on Sep. 12, 2007, for International Application No. PCT/AU2007/000903.

*Primary Examiner* — David Rogers
(74) *Attorney, Agent, or Firm* — Sheridan Ross P.C.

(57) ABSTRACT

The present invention provides a device (10) for detecting the frothing ability of a fluid, said device including: an inlet (11) for receiving a portion of said fluid; means (12) for entraining air into said fluid portion; a mixing chamber (13) for receiving said air entrained fluid portion, said mixing chamber (13) being adapted for mixing said fluid portion and said air; and a detector (15) for detecting the amount of froth (18) generated in said mixing chamber (13). The invention also provides a method for detecting the frothing ability of a fluid.

45 Claims, 5 Drawing Sheets

U.S. PATENT DOCUMENTS

| | | | |
|---|---|---|---|
| 5,182,014 A * | 1/1993 | Goodman | 209/164 |
| 5,249,688 A * | 10/1993 | Hwang | 209/170 |
| 5,307,937 A * | 5/1994 | Hutwelker | 209/164 |
| 5,368,166 A * | 11/1994 | Chumak et al. | 209/168 |
| 5,431,286 A * | 7/1995 | Xu et al. | 209/170 |
| 5,465,610 A * | 11/1995 | Loisel | 73/60.11 |
| 5,511,669 A * | 4/1996 | Bourke | 209/164 |
| 5,597,950 A * | 1/1997 | Mullen | 73/60.11 |
| 5,702,612 A * | 12/1997 | Wang | 210/703 |
| 5,746,910 A * | 5/1998 | Negeri | 209/168 |
| 5,876,558 A * | 3/1999 | Deng et al. | 162/4 |
| 6,073,775 A * | 6/2000 | Liu | 209/170 |
| 6,397,665 B1 * | 6/2002 | Kirts et al. | 73/60.11 |
| 6,959,815 B2 * | 11/2005 | Xu et al. | 209/166 |
| 7,152,741 B2 * | 12/2006 | Jara et al. | 209/166 |
| 7,770,455 B2 * | 8/2010 | Stencel | 73/589 |
| 2001/0042407 A1 * | 11/2001 | Kirts et al. | 73/579 |
| 2003/0106843 A1 * | 6/2003 | Jameson et al. | 209/162 |
| 2005/0051465 A1 * | 3/2005 | Khan et al. | 209/162 |

FOREIGN PATENT DOCUMENTS

| | | |
|---|---|---|
| EP | 0655610 A2 | 5/1995 |
| JP | 8305852 A | 11/1996 |
| JP | 2002055099 A * | 2/2002 |
| SU | 1789281 A2 * | 1/1993 |
| WO | WO 92/22799 A | 12/1992 |
| WO | WO 00/68672 A1 | 11/2000 |
| WO | WO 01/38001 A1 | 5/2001 |
| WO | WO 2004/077008 A2 | 9/2004 |
| WO | WO 2006081611 * | 8/2006 |

* cited by examiner

DEVICE AND METHOD FOR DETECTING THE FROTHING ABILITY OF A FLUID

CROSS REFERENCE TO RELATED APPLICATIONS

This application is a national stage application under 35 U.S.C. 371 of PCT Application No. PCT/AU2007/000903 having an international filing date of 29 Jun. 2007, which designated the United States, which PCT application claimed the benefit of Australian Application No. 2006903676 filed 30 Jun. 2006, the entire disclosures of which are hereby incorporated herein by reference.

FIELD OF THE INVENTION

This present invention relates to a device and method for detecting the frothing ability of a fluid, and in particular, a device and method for detecting residual frother in a liquid stream in a minerals separation process.

The invention has been developed primarily for use in detecting residual frother in a coal separation process, and will be described hereinafter with reference to this application. However, it will be appreciated that the invention is not limited to this particular field of use. In particular, it is contemplated that the invention is applicable to a separation process using a frother for any mineral, including iron ore, copper and lead. It is also contemplated that the invention is applicable to any field where detecting the frothing ability of a fluid is required.

BACKGROUND OF THE INVENTION

Any discussion of the prior art throughout the specification should in no way be considered as an admission that such prior art is widely known or forms part of the common general knowledge in the field.

Coal processing plants typically employ one or more minerals separation flotation cells to process fine coal. A slurry or pulp containing coal and gangue is fed into the flotation cell or cells, which separate the coal values or concentrates from the gangue by inducing bubbles so that the values float to the surface of the pulp. The coal values are recovered by an overflow weir or launder as a product stream, whereas the gangue is drained from the lower part of the cell as a tailings stream. To facilitate separation and improve the productivity of the floatation cells, typically surfactants and wetting agents are used as "frother" to encourage the production of bubbles or "froth" for transporting the coal values to the pulp surface. An example of a frother is methyl isobutyl carbinol (MIBC).

Whilst frother assists in the flotation process, it acts as a contaminant in the tailings stream and poses an environmental pollutant if it is discharged into the tailings dam. Furthermore, the tailings stream is often recycled to obtain clarified water for use in the pumping system of the rest of the processing plant. The presence of too much frother in the tailings stream contaminates the clarified water, since excess frother causes cavitations in the pumping system and "froths out" the coal processing plant. Flushing the frother out of the pumping system requires the shut down of the entire plant and the associated down time spent in cleaning out the pump system results in wasted labour and lost production.

This problem is exacerbated by the presence of other substances in the tailings stream, such as dissolved salts and some solids, which also facilitate the formation of froth in the liquid.

In this context, coal separation by flotation typically involves only 20% of the coal produced by the entire coal processing plant and is limited to the recovery of fine coal, whereas the rest of the plant produces the remaining 80% of the coal. Consequently, to avoid these potential production losses and environmental hazards, it has been the practice to use substantially reduced amounts of frother in the flotation cells to minimize the presence of frother in the tailings stream. This, however, reduces the efficiency of the flotation cells in recovering fine coal.

SUMMARY OF THE INVENTION

According to one aspect of the invention, there is provided a device for detecting the frothing ability of a fluid, said device including:
  an inlet for receiving a portion of said fluid;
  means for entraining air into said fluid portion;
  a mixing chamber for receiving said air entrained fluid portion, said mixing chamber being adapted for mixing said fluid portion and said air; and
  a means for displaying the amount of froth generated in said mixing chamber.

Another aspect of the invention provides a method for detecting the frothing ability of a fluid, said method including the steps of:
  obtaining a portion of said fluid;
  entraining air into said fluid portion;
  mixing said air and said fluid portion; and
  displaying the amount of froth generated by said mixing step.

Throughout this specification, the term "froth" includes bubbles, foam and any agglomeration thereof, and the term "frothing agent" means any substance which encourages the formation of froth in a fluid or a liquid, including frother, chemicals, dissolved salts and solids.

Preferably, the air entraining means entrains air at a controlled rate. Preferably, the air entraining means is adapted for fluidly injecting said fluid portion. Preferably, the air entraining means includes an aerator, an aspirator, a sparger, a nozzle or a Venturi-type tube.

Preferably, the air entraining means includes a nozzle adapted for fluidly injecting said fluid portion such that said fluidly injected fluid portion entrains air adjacent said nozzle. Preferably, the nozzle has sidewalls converging or tapering to a nozzle aperture. Preferably, the nozzle has a generally geometrical or polygonal cross-section. Preferably, the nozzle has a frusto-conical shape. Preferably, the air entraining means includes a port for introducing air adjacent said nozzle. Preferably, said port is located adjacent said nozzle.

Preferably, the mixing chamber is adapted to agitate the entrained air and the fluid portion. Preferably, the mixing chamber includes a restriction for restricting fluid flow therein. Preferably, the restriction at least partially forms an outlet of the mixing chamber. Preferably, the mixing chamber is substantially tubular in shape. Preferably, wherein the mixing chamber has a generally geometrical or polygonal cross-section. Preferably, wherein the mixing chamber is a downcomer.

Preferably, the device includes a conduit for conveying said air entrained fluid portion and/or froth from said mixing chamber to said display means. Preferably, the conduit forms part of the mixing chamber. Preferably, the conduit is a U-shaped tube. Preferably, the tube includes an angled portion.

In an alternative embodiment, the mixing chamber terminates in an outlet and a tank adapted for receiving the air entrained fluid portion and/or froth. Preferably, the tank includes an open top forming the display means.

Preferably, the mixing chamber or conduit includes an outlet. Preferably, the outlet includes a valve for controllably discharging said fluid portion and said froth.

Preferably, the display means is associated with the mixing chamber. Preferably, the display means is integrally formed with the mixing chamber. Preferably, the display means includes the outlet of the mixing chamber or conduit. Preferably, the display means includes a visual monitoring unit. Preferably, the visual monitoring unit includes a camera.

Preferably, the device includes a unit for measuring the frothing ability of the fluid. Preferably, the measuring unit includes one or more sensors to measure one of more parameters of the device and/or fluid. Preferably, the parameters include one or more of the following: fluid feed pressure, fluid feed temperature, air flow rate, air vacuum, bubble size or diameter, nozzle diameter, nozzle shape, mixing chamber diameter and the mixing chamber shape. Preferably, the measuring unit includes a central processing unit to calculate the frothing ability of the fluid from the measured parameters.

Preferably, the air entraining step includes entraining air at a controlled rate. Preferably, the air entraining step includes forcing said fluid portion through a constricted passage to entrain air. Preferably, the air entraining step includes introducing air adjacent the passage. Preferably, the air entraining step includes fluidly injecting said fluid.

Preferably, the mixing step includes mixing the air entrained fluid in a mixing chamber. Preferably, the mixing step includes agitating the air entrained fluid to generate froth.

Preferably, the displaying step includes visually detecting said froth.

Preferably, the obtaining step includes diverting said fluid portion from a fluid stream.

Preferably, the method further includes the step of measuring said froth. Preferably, said measuring step includes measuring one or more of the following parameters: fluid feed pressure, fluid feed temperature, air flow rate, air vacuum, bubble size or diameter, nozzle diameter, nozzle shape, mixing chamber diameter, and mixing chamber shape.

Preferably, the fluid is from a fluid stream of a minerals separation process. Preferably, the fluid stream includes a tailings stream, a product stream, a circulating medium stream, a clarified water stream, clarified water or other liquid stream. In a particular application of the invention, the fluid stream includes the circulating medium or dense medium feedstreams of a coal processing plant.

BRIEF DESCRIPTION OF THE DRAWINGS

Preferred embodiments of the invention will now be described, by way of example only, with reference to the accompanying drawings, in which.

PREFERRED EMBODIMENTS OF THE INVENTION

Figure 1:
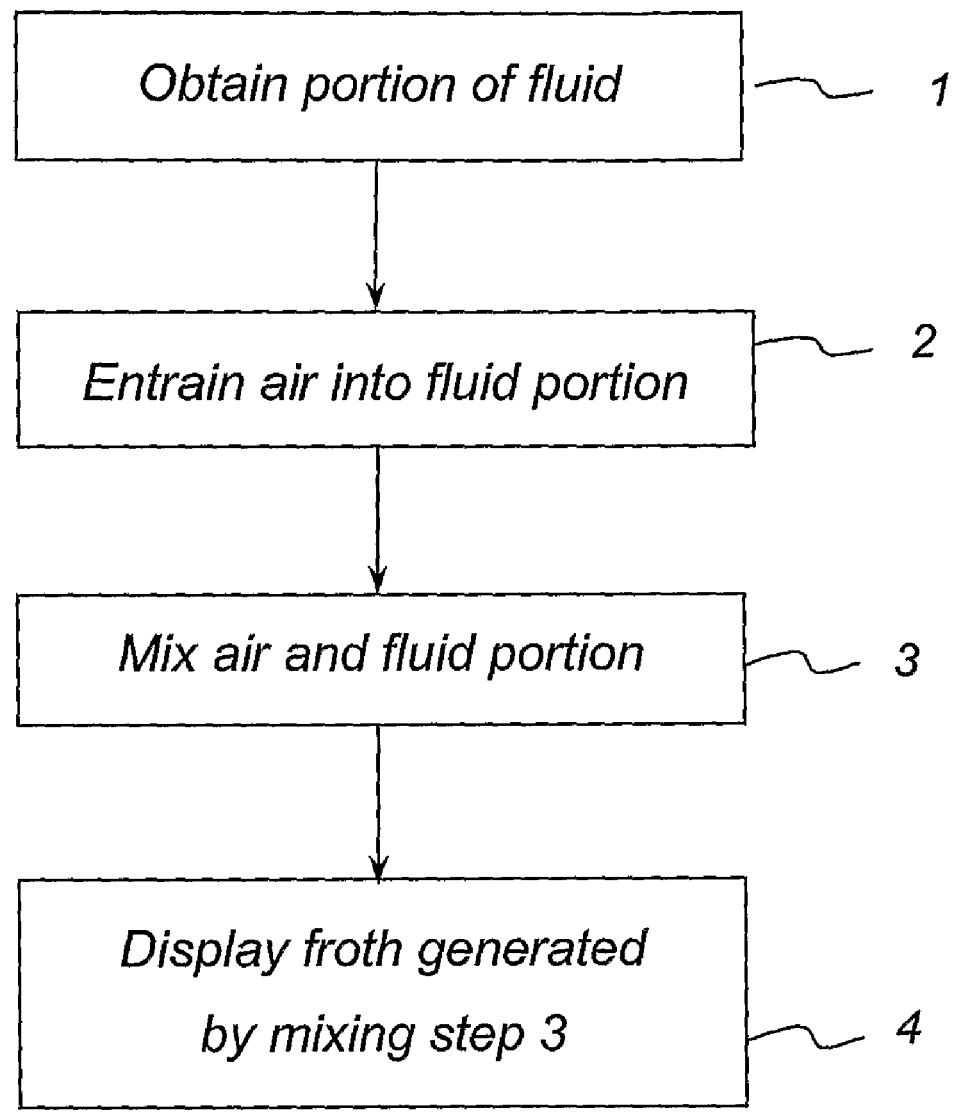
FIG. 1 is a schematic drawing illustrating a method according to one embodiment of the invention.

Referring to FIG. 1, a method for detecting the frothing ability of a fluid includes the steps of obtaining a portion of the fluid at step 1 and entraining air into the fluid portion at step 2. At step 3, the entrained air and the fluid portion are mixed and at step 4 the amount of froth generated by the mixing step 3 is displayed to provide an indication of the frothing ability of the fluid.

The method is implemented by diverting the fluid portion from a fluid stream to take a representative sample and detect the ability of the fluid portion to generate froth by determining the presence of any frothing agents, including frother, present in the fluid. The fluid stream is any one of the various feed, circulating medium, product and tailings streams of a minerals separation process, such as a froth flotation process employing Jameson-type flotation cells. The circulating medium stream includes the clarified water stream recycled for use in the rest of the coal plant via a pumping system.

By monitoring the ability of the fluid to generate froth, the amount of frother that is added into the system can be controlled, permitting the optimum use of frother without increasing the risk of "frothing out" the system. In addition, the method also takes into account the presence of frothing agents other than known frother, such as any dissolved salts and the effect of solids in the fluid stream, and any substances which may hinder the formation of froth known as "froth hindering agents", such as diesel and oil.

Figure 2:
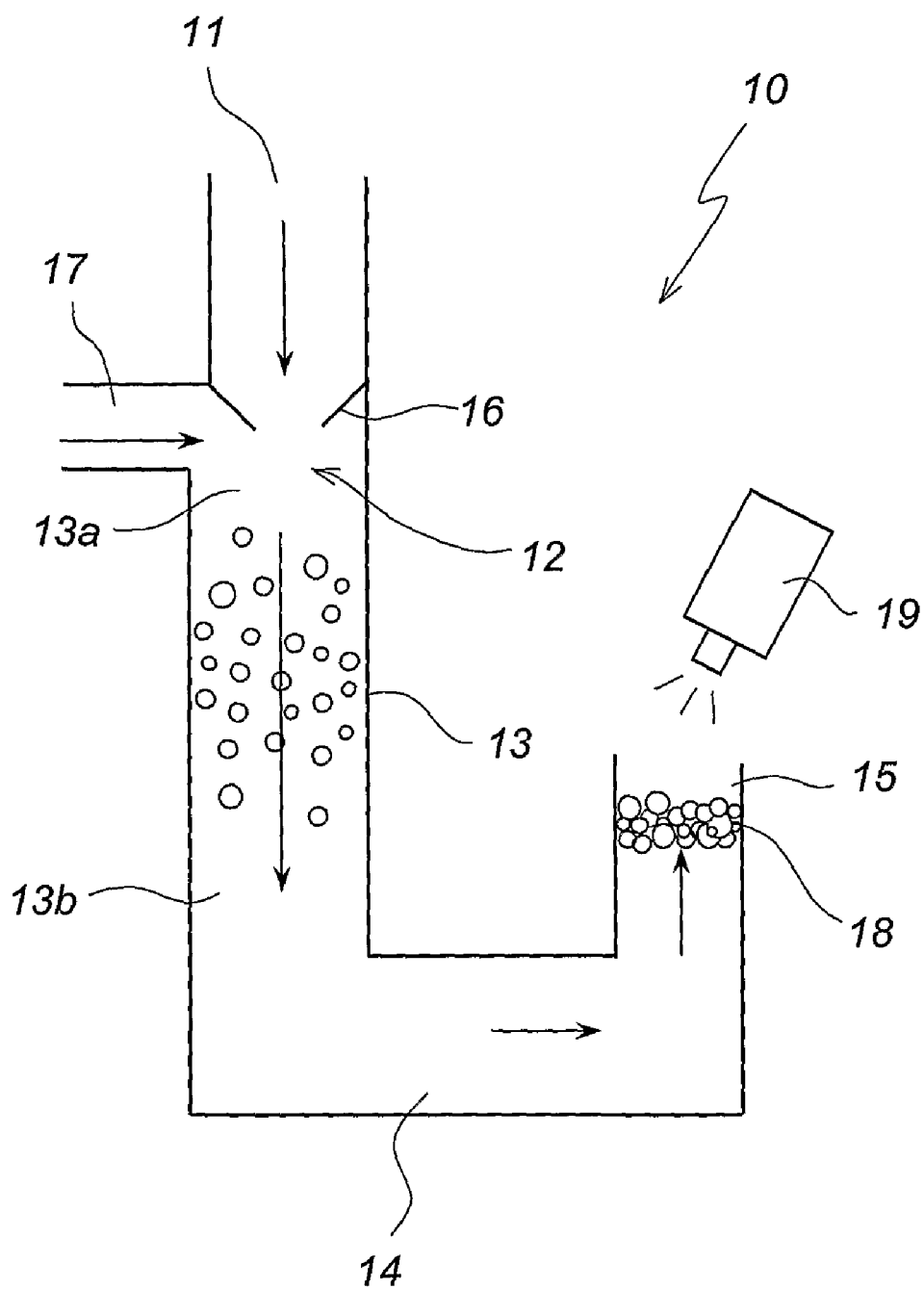
FIG. 2 is a schematic drawing of a device according to one embodiment of the invention.

Referring to FIG. 2, a device 10 for detecting the frothing ability of a fluid includes an inlet 11 for receiving a portion of the fluid, which in this embodiment is liquid from a tailings stream of a coal processing plant. The device 10 further includes means 12 for entraining air into the liquid portion and a mixing chamber 13, which is adapted for mixing the liquid portion and entrained air. A tubular U-shaped conduit 14 ensures that the mixing chamber 13 is kept full and a means 15 in the form of an outlet displays the amount of froth generated in the mixing chamber 13. The air entraining means 12 includes a frusto-conical nozzle 16 adapted for fluidly injecting the liquid from the inlet 11 into the mixing chamber 13 and a port 17 located adjacent the nozzle 16 for introducing air in proximity to the nozzle 16. That is, air is entrained into the liquid portion as it enters the mixing chamber 13 by the action of the fluid jet created by the nozzle 16. The greater the frothing ability of the liquid, the more air that is entrained into the liquid portion.

The air entrained liquid portion is then transported into the mixing chamber 13 to facilitate the formation of froth. The mixing chamber 13 is in the form of a downcomer tube generally having a transport zone 13a, where the air entrained liquid is moving under the action of the fluid jet, and a mixing zone 13b, where any frother or other frothing agents contained within the liquid portion reacts with the entrained air and liquid portion to create froth 18. The froth 18 and liquid then exits the mixing tube 13 into the U-shaped conduit 14 for transport to the outlet 15, where the appearance and amount of the froth 18 that is formed in the mixing tube 13 is displayed.

In addition, a detector 19 in the form of a closed circuit camera monitors the outlet 15 to transmit the visual image of the froth 18 to the control room of the flotation cell system so that an operator obtains a quick visual indication as to the presence and amount of froth visible at the outlet 15. This allows the operator to determine whether there is any excess frother left in the tailings stream from the flotation cell process, since the amount of any other frothing agents in the tailings stream is relatively fixed compared with the amount of residual frother. In response to this visual indication, the operator controls the dosage rate of the frother into the flotation cells, so that the optimum amount of frother is added to the system, maximizing flotation cell performance while minimizing the risk of adversely impacting the performance of the processing plant by the presence of excess frother and frothing agents in the tailings stream of the flotation cell system.

Employing a camera 19 not only provides a visual indication of the froth 18 produced in the mixing tube 13, but also confers the benefit of gauging the performance of the flotation cells by permitting visual examination of the colour and "feel" of the discharge from the outlet 15.

Figure 3A:
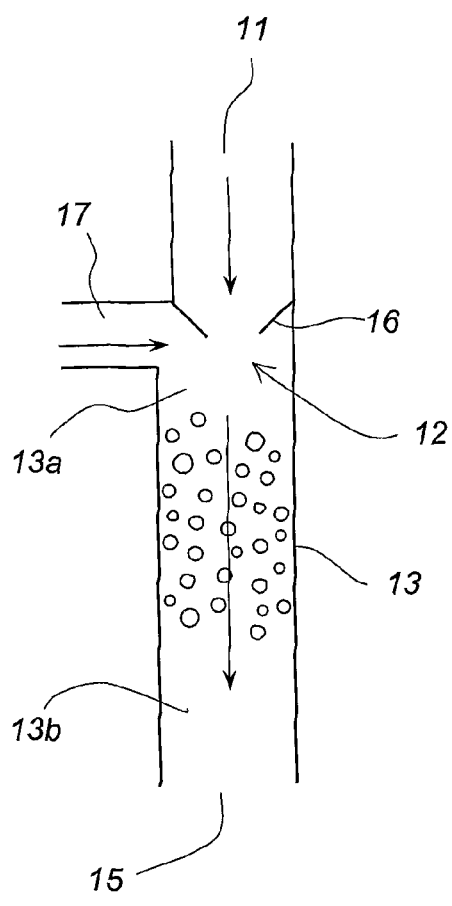
FIGS. 3A and 3B are schematic drawings of alternative configurations of the mixing chamber for the device of FIG. 2.
Figure 3B:
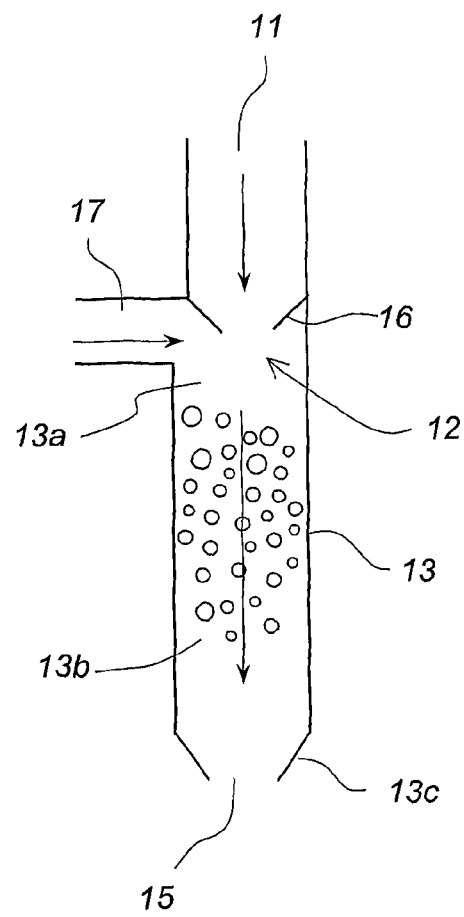

Whilst the mixing chamber/tube 13 has been shown as being integrally formed with the U-shaped conduit 14, it will be appreciated by one skilled in the art that the mixing chamber 13 can be configured in several ways to achieve mixing of the entrained air and liquid, thus inducing formation of froth. Example of such variations are illustrated in FIGS. 3A and 3B, where corresponding features have been given the same reference numerals. In FIG. 3A, the mixing chamber 13 is a cylindrical tube with an open end 15 forming the outlet, whereas in FIG. 3B, where the mixing chamber 13 includes a restriction 13c forming the outlet 15. In both cases, it is not necessary to provide a conduit, container or the like to capture the mixture of froth and liquid from the outlet 15. The restriction 13c impedes the flow of the air entrained liquid, ensuring that sufficient liquid is retained in the mixing chamber 13 to achieve the necessary mixing of entrained air and liquid to generate froth. Thus, a conduit, container or the like is not required. Similarly, the mixing chamber 13 of FIG. 3A would be typically used where there is a sufficiently high flow velocity in the fluid that a restriction or conduit to retain the liquid for mixing is not required.

Figure 4:
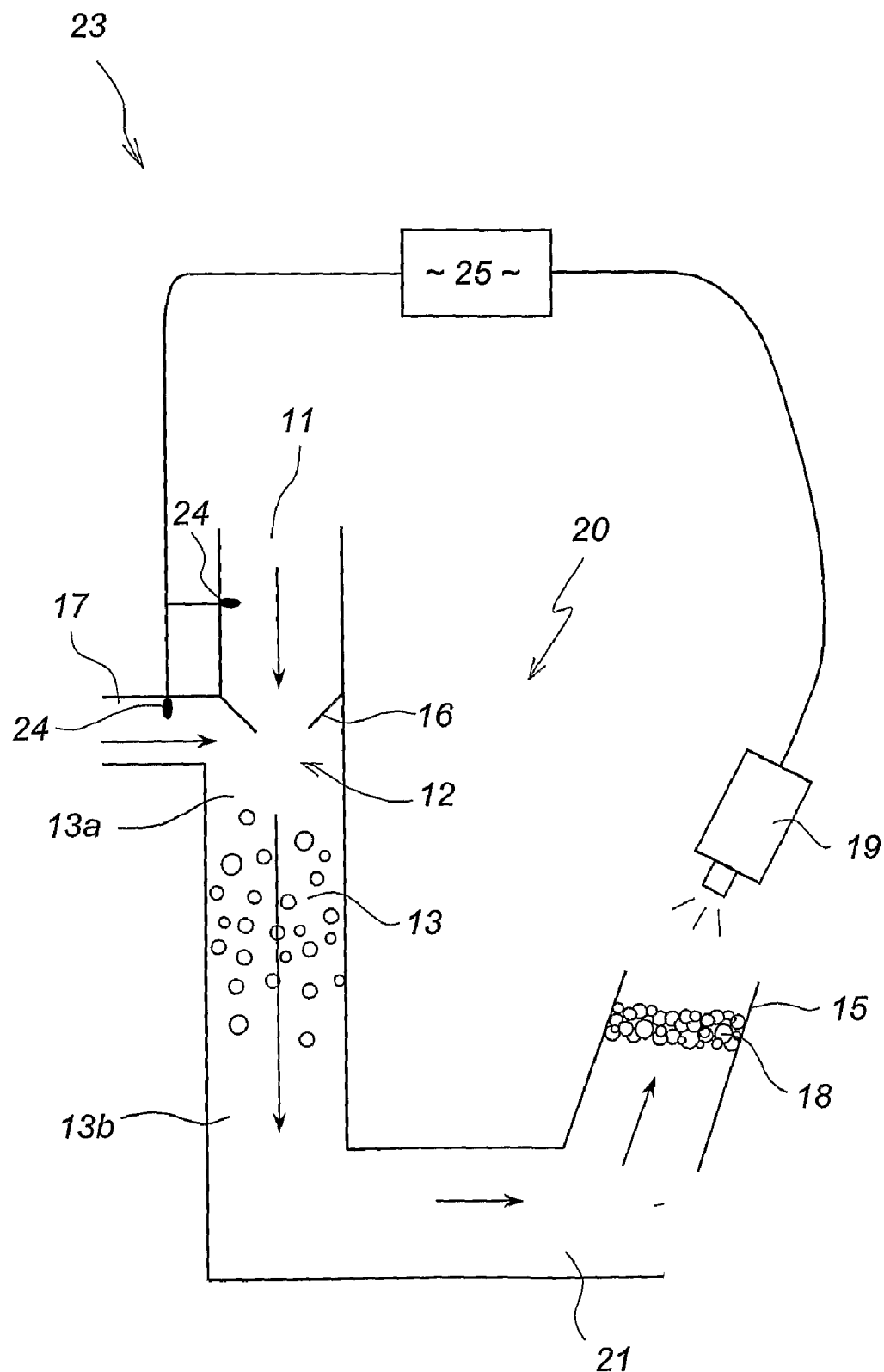
FIG. 4 is a schematic drawing of a device according to another embodiment of the invention.

Another embodiment of the device is illustrated in FIG. 4, where corresponding features have been given the same reference numerals. The device 20 has the substantially similar air entraining means 12 with a frusto-conical nozzle 16 and an associated port 17 for introducing air in proximity to the nozzle 16, and operates in a substantially same manner as the device 10 of FIG. 2. The differences between this embodiment and the embodiment of FIG. 2 are that the U-shaped tube 21 has been reconfigured as an angled tube, with a tube portion 22 at an angle with respect to the downcomer 13, and the provision of a measuring unit 23.

The measuring unit 23 measures the frothing ability caused by the presence of frothing agents, including residual frother, in the liquid portion sampled from the tailings stream by the device 20. The measuring unit 23 includes sensors 24 and a central processing unit (CPU) 25. The sensors 24 measure the liquid feed pressure at the inlet 11 and the air flow rate and air vacuum at the port 17, being the operational parameters of the device 20. The CPU 25 then uses these measured values together with the known geometrical parameters of the device 20 to calculate the frothing ability of the liquid in question. The geometrical parameters of the device 20 include the nozzle diameter, nozzle shape, mixing tube diameter and mixing tube shape.

Where one or more of these operational parameters are constant, then the measuring system 23 only needs to measure the variable parameter(s) to calculate the frothing ability of the liquid. For example, if the liquid feed pressure at the inlet 11 and the air vacuum at the port 18 were constant, then the air flow rate measured at the port 17 by the sensor 24 will be proportional to the frothing ability of the liquid. As another example, if the liquid feed pressure was constant, then the air flow rate and the air vacuum would provide a measurement of the frothing ability of the liquid. Although the geometrical parameters are typically constant, one or more of these parameters could be varied in a further embodiment, such as where the nozzle has an adjustable diameter. In this case, if the feed liquid pressure, air vacuum and air flow rate were constant, then the variable geometrical parameter of the nozzle diameter would be measured to determine the frothing ability of the liquid.

In one embodiment, measurement is accomplished by providing a camera to determine the size or diameter of the froth/bubbles in the conduit 14, 21 after leaving the mixing chamber 23. In general, the frothing propensity of the fluid is inversely proportional to the bubble diameter; that is, the higher the level of frothing propensity, the smaller the bubble diameter. Measuring the bubble size or diameter provides an alternative to measuring the air flow and vacuum, since a smaller bubble diameter tends to indicate a higher air flow and/or vacuum. It is contemplated that this embodiment is particularly applicable where the device is used to measure or detect the frothing ability of clarified water or any other transparent liquid, where it would be easier to visually detect or measure the bubble size online through the camera.

It will be appreciated by one skilled in the technical field that not all these variable parameters need to be measured to determine the frothing ability of the fluid. For example, the temperature of the feed fluid may be measured instead of, or in addition to, the feed fluid pressure. Moreover, the device is typically calibrated on-site so as to be tailored to the system for which the device is to be used.

Figure 5:
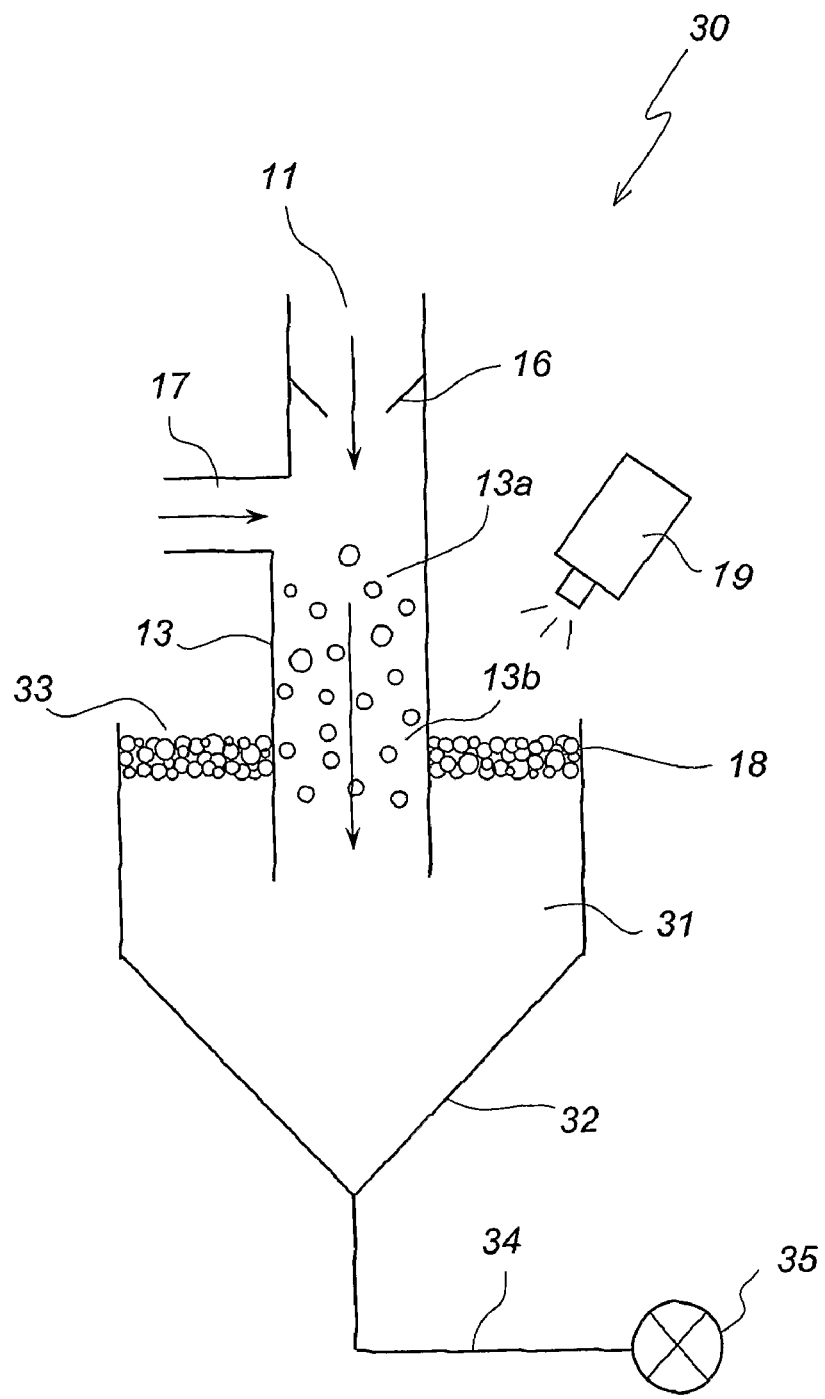
FIG. 5 is a schematic drawing of a device according to a further embodiment of the invention.

Referring to FIG. 5, a further embodiment of the invention is shown, where corresponding features have been given the same reference numerals. The variation in this device 30 involves the reconfiguration of the conduit 14 and the outlet 15 as an open tank 31 with a frusto-conical bottom 32. In addition, the port 17 for introducing air into the device 30 is displaced from the nozzle 16, but is sufficiently proximate for the fluid jet to entrain air as it flows along the downcomer 13. The open top 33 of the tank 31 acts as an outlet to enable visual detection of the froth 18 by the camera 19. A conduit 34 leads to a drainage outlet 35 to enable drainage of the tank 31. Aside from the variation in the configuration of the tank 31 and the location of the port 17, the device 30 operates in a substantially similar manner as the devices 10 and 20 of FIGS. 2 and 3, respectively.

It will be appreciated by one skilled in the art that the mixing chambers of FIGS. 3A and 3B can be readily substituted for the mixing chambers 13 in the devices 20, 30 of FIGS. 4 and 5.

In the embodiments, the nozzle has been described as being frusto-conical, with the mixing chamber and conduit being cylindrically tubular in shape. However, it will be appreciated that the nozzle, mixing chamber and conduit may each vary in shape. For example, the nozzle may be frustum-like; that is, the sidewalls of the nozzle converge or taper to the nozzle aperture, with the cross-section of the nozzle being any polygonal or geometrical shape, such as rectangular, triangular, hexagonal, pentagonal, circular, oval or square. Similarly, the mixing chamber and the conduit may each also adopt any geometrical or polygonal cross-sectional-shape. For example, the mixing chamber may have a geometrical or polygonal cross-section, examples of which are discussed above, rather than a circular cross-section. Thus, the mixing chamber is not limited to a cylindrical tube. Likewise, the conduit is also not limited to a cylindrical tubular shape and may have a geometrical or polygonal cross-section, examples of which are discussed above. Moreover, the shapes of the mixing chamber, conduit and the nozzle can be combinations of any of these geometrical shapes. In addition, there is no limitation that the shapes of the nozzle, mixing chamber or conduit in the device have to be uniform, and each of these components can adopt different shapes with respect to each other.

It will be appreciated that the preferred embodiments of the invention describe a method and device for measuring the frothing ability of a liquid from the tailings stream of a coal separation flotation process. This enables optimization in the performance of the flotation cells whilst reducing the risk of residual frother and any other frothing agents in the tailings stream adversely affecting the performance of the rest of the coal processing plant. Furthermore, the devices are able to detect not only presence of frother, but also any other potential frothing agents, such as dissolved salts, or a combination of dissolved salts and frother, in the tailings stream. Thus, if a known frother, other frothing agents or a combination of both are added to the coal processing plant, then the amount of frother and frothing agents can be calibrated into the operation of the coal processing plant. In addition, the presence of any froth hindering agents, such as diesel or oil, can also be calibrated into the system. These advantages conferred by the invention are equally applicable to other fluid streams, such as product streams, medium dense streams, circulating medium streams, and especially to clarified water streams that are recycled for use in other parts of the plant. The invention is also generally applicable to other fluid streams where the amount of froth produced by any frothing agents needs to be monitored or measured.

In other embodiments, a valve is provided at the outlet 15 to control the discharge of the froth 18 and the liquid. The detector 19 and/or the measuring unit 23 may be associated with the valve. Other embodiments use an aerator, an aspirator, a sparger or a Venturi-type tube to entrain air in the fluid portion. Further embodiments use different geometrical configurations for the mixing chamber and/or nozzle to promote mixing of the entrained air and the fluid portion, such as rectangular, square, hexagonal, pentagonal, oval or other suitable polygonal cross-sections. A further embodiment does not employ a camera 19 or other visual detector to monitor the outlet 15, and the operator may simply inspect the outlet 15 whilst checking the flotation cell system to gauge the amount of frothing agents in the fluid. In yet another embodiment, several of the devices are provided to detect the frothing ability of the fluid in two or more of the fluid streams of a mineral processing plant, including the product stream, tailings stream, circulating medium stream and clarified water stream. Moreover, the invention is also applicable to any separation process using a frother or frothing agent, and extends to processes for separating other minerals, such as iron ore, copper and lead.

In many applications of the invention, the actual amount of frother is not required to be determined. What is often required is to find a limit of the amount of froth that can be permitted so that the operation of the rest of the coal processing plant will not impaired. In such cases, the plant would be operated and when the plant performance is impacted upon by the presence of frothing agents, especially frother, in the tailings stream, the amount of froth detected or measured by the devices 10, 20, 30 would be recorded, and the flotation cells would be operated so as not to exceed this value.

Although the invention has been described with reference to specific examples, it will be appreciated by those skilled in the art that the invention may be embodied in many other forms.

The invention claimed is:

1. A device for detecting the frothing ability of a fluid, said device comprising:
an inlet for receiving a portion of said fluid;
means for entraining air into said fluid portion;
a mixing chamber for receiving said air entrained fluid portion, said mixing chamber being adapted for mixing said fluid portion and said air;
means for displaying the amount of froth generated in said mixing chamber; and
the device includes a unit for measuring the frothing ability of the fluid.

2. The device of claim 1, wherein said air entraining means entrains air at a controlled rate.

3. The device of claim 1, wherein said air entraining means is adapted for fluidly injecting said fluid portion adjacent to said inlet.

4. The device of claim 1, wherein said air entraining means includes an aerator, an aspirator, a sparger, a nozzle or a Venturi-type tube.

5. The device of claim 1, wherein the mixing chamber is substantially tubular in shape.

6. The device of claim 1, wherein the mixing chamber has a generally geometrical cross-section.

7. The device of claim 1, wherein the mixing chamber is a downcomer.

8. The device of claim 1, wherein said air entraining means includes a nozzle adapted for fluidly injecting said fluid portion such that said fluidly injected fluid portion entrains air adjacent said nozzle.

9. The device of claim 8, wherein said air entraining means includes a port for introducing air adjacent said nozzle.

10. The device of claim 9, wherein the port is located adjacent said nozzle.

11. The device of claim 8, wherein the nozzle has sidewalls converging or tapering to a nozzle aperture.

12. The device of claim 11, wherein the nozzle has a generally geometrical cross-section.

13. The device of claim 12, wherein the nozzle has a frusto-conical shape.

14. The device of claim 1, wherein the mixing chamber is adapted to agitate the entrained air and the fluid portion.

15. The device of claim 11, wherein the mixing chamber includes a restriction for restricting fluid flow therein.

16. The device of claim 15, wherein the restriction at least partially forms an outlet of the mixing chamber.

17. The device of claim 14, wherein the mixing chamber terminates in an outlet and a tank adapted for receiving the air entrained fluid portion and/or froth.

18. The device of claim 17, wherein the tank includes an open top forming the means for display.

19. The device of claim 1, wherein the device includes a conduit for conveying said air entrained fluid portion and/or froth from said mixing chamber to said display means.

20. The device of claim 19, wherein the conduit forms part of the mixing chamber.

21. The device of claim 19, wherein the conduit is a U-shaped tube.

22. The device of claim 21, wherein the tube includes an angled portion.

23. The device of claim 19, wherein the mixing chamber or conduit includes an outlet.

24. The device of claim 23, wherein the outlet includes a valve for controllably discharging said fluid portion and said froth.

25. The device of claim 23, wherein the means for display includes the outlet of the mixing chamber or conduit.

26. The device of claim 1, wherein the means for display is associated with the mixing chamber.

27. The device of claim 26, wherein the means for display is integrally formed with the mixing chamber.

28. The device of claim 1, wherein the means for display includes a visual monitoring unit.

29. The device of claim 28, wherein the visual monitoring unit includes a camera.

30. The device of claim 1, wherein the measuring unit includes one or more sensors to measure one or more parameters of the device and/or fluid.

31. The device of claim 30, wherein the parameters comprise at least one of a fluid feed pressure, a fluid feed temperature, an air flow rate, an air vacuum, a bubble size or diameter, a nozzle diameter, a nozzle shape, a mixing chamber diameter and a mixing chamber shape.

32. The device of claim 30, wherein the measuring unit includes a central processing unit to calculate the frothing ability of the fluid from the measured parameters.

33. The device of claim 1, wherein said fluid is from a fluid stream of a minerals separation flotation process.

34. The device of claim 33, wherein the fluid stream includes a tailings stream, a feed stream, circulating medium stream, a product stream or a clarified water stream.

35. A method for detecting the frothing ability of a fluid, said method comprising:
  obtaining a portion of said fluid;
  entraining air into said fluid portion;
  mixing said air and said fluid portion;
  displaying the amount of froth generated by said mixing step; and
  measuring one or more parameters of said froth, said parameters comprising at least one of a fluid feed pressure, a fluid feed temperature, an air flow rate, an air vacuum, a bubble size or diameter, a nozzle diameter, a nozzle shape, a mixing chamber diameter, and a mixing chamber shape.

36. The method of claim 35, wherein the air entraining step includes entraining air at a controlled rate.

37. The method of claim 35, wherein the air entraining step includes fluidly injecting said fluid.

38. The method of claim 35, wherein the mixing step includes mixing the air entrained fluid in a mixing chamber.

39. The method of claim 35, wherein the mixing step includes agitating the air entrained fluid to generate froth.

40. The method of claim 35, wherein the displaying step includes visually detecting said froth.

41. The method of claim 35, wherein the obtaining step includes diverting said fluid portion from a fluid stream.

42. The method of claim 35, wherein the air entraining step includes forcing said fluid portion through a constricted passage to entrain air.

43. The method of claim 42, wherein the air entraining step includes introducing air adjacent the passage.

44. The method of claim 35, wherein said fluid is from a fluid stream of a minerals separation flotation process.

45. The method of claim 44, wherein the fluid stream includes a tailings stream, a product stream, a circulating medium stream or a clarified water stream.

* * * * *